United States Patent
Webster

(10) Patent No.: US 6,737,649 B2
(45) Date of Patent: May 18, 2004

(54) INFRARED ANALYSIS INSTRUMENT WITH OFFSET PROBE FOR PARTICULATE SAMPLE

(75) Inventor: Donald R. Webster, Laurel, MD (US)

(73) Assignee: Foss NIRSystems, Inc., Silver Spring, MD (US)

( * ) Notice: Subject to any disclaimer, the term of this patent is extended or adjusted under 35 U.S.C. 154(b) by 0 days.

(21) Appl. No.: 10/122,373

(22) Filed: Apr. 16, 2002

(65) Prior Publication Data

US 2003/0193028 A1 Oct. 16, 2003

(51) Int. Cl.[7] ............................................. G01N 21/01
(52) U.S. Cl. ........................... 250/339.07; 250/339.01; 356/301
(58) Field of Search ................... 250/339.07, 339.01, 250/339.02, 339.09, 339.11, 339.12, 341.8; 356/301

(56) References Cited

U.S. PATENT DOCUMENTS

| | | | |
|---|---|---|---|
| 4,573,761 A | | 3/1986 | McLachlan |
| 4,758,065 A | | 7/1988 | Dorman |
| 4,921,326 A | | 5/1990 | Wild |
| 5,112,127 A | * | 5/1992 | Carrabba et al. ............ 356/301 |
| 5,262,644 A | * | 11/1993 | Maguire ................. 250/339.08 |
| 5,293,872 A | * | 3/1994 | Alfano et al. ............... 600/475 |
| 5,402,508 A | | 3/1995 | O'Rourke |
| 5,410,413 A | | 4/1995 | Sela |
| 5,436,454 A | * | 7/1995 | Bornstein et al. ........ 250/339.12 |
| 5,525,800 A | * | 6/1996 | Sanghera et al. ........ 250/339.08 |
| 5,569,923 A | | 10/1996 | Weissman |
| 5,754,715 A | | 5/1998 | Melling |
| 5,773,835 A | | 6/1998 | Sinofsky |
| 5,841,545 A | | 11/1998 | Young |
| 5,911,017 A | | 6/1999 | Wach |
| 5,952,660 A | * | 9/1999 | Kip et al. ............... 250/339.11 |
| 5,986,755 A | * | 11/1999 | Ornitz et al. ................ 356/301 |
| 6,076,009 A | | 6/2000 | Raylman |
| 6,208,887 B1 | | 3/2001 | Clarke |
| 6,411,907 B1 | * | 6/2002 | Lu et al. ......................... 702/28 |
| 6,430,513 B1 | * | 8/2002 | Wang et al. .................. 702/28 |

* cited by examiner

Primary Examiner—Constantine Hannaher
Assistant Examiner—Otilia Gabor
(74) Attorney, Agent, or Firm—Andrew C. Aitken; Venable LLP

(57) ABSTRACT

In an infrared analysis instrument, a fiber optic probe, designed to be inserted into a particulate sample, is formed from distal ends of transmitting and receiving optic fibers. The distal ends of the transmitting fibers are located centrally in the probe and the distal ends of the receiving fibers are formed in a ring around the distal ends of the transmitting fibers. The distal ends of the receiving fibers are set back from the distal ends of the transmitting fibers. The receiving fibers carrying diffusely scattered light reflected from and transmitted through the particulate sample to a spectrophotometer housing containing fixed grating and an array of silicon photodetectors arranged to detect the spectrum dispersed by the grating in the range of 500 to 1100 nm.

13 Claims, 2 Drawing Sheets

INFRARED ANALYSIS INSTRUMENT WITH OFFSET PROBE FOR PARTICULATE SAMPLE

This invention relates to near infrared analysis instruments and more particularly to instruments of rugged design for field use for analysis of particulate material.

A powerful technology for analyzing or identifying material involves measuring the reflectance from or the transmission through the material to be analyzed at narrow wavelength bands in the near infrared range, known as NIR. A typical analyzing instrument comprises a spectrophotometer employing a grating to disperse the infrared light into a spectrum to enable the absorption of the matter to be measured at narrow wavelength bands. In one type of instrument, broad band NIR is dispersed into a spectrum by an oscillating grating. As the grating oscillates, the wavelength of the dispersed light passing through an exit slit is scanned through the spectrum. The infrared light passing though the exit slit irradiates a sample of material to be analyzed. The light transmitted through the sample or reflected from the sample is detected to obtain a measurement of the absorption spectrum of the sample. Alternatively the broad band NIR may irradiate the sample, in which case the light reflected from the sample or transmitted through the sample is directed to the grating to be dispersed to obtain the absorption spectrum measurements. In another type of spectrophotometer, a fixed grating is used to disperse the infrared light into a spectrum, which is detected by an array of photodetectors each positioned and shaped to detect a narrow band of the dispersed spectrum. In this kind of instrument, the sample is irradiated with broad band NIR and the light transmitted through or reflected from the sample is dispersed by the fixed grating into the spectrum detected by the array of photodetectors.

An instrument with a fixed grating array would be preferred for field use because it is more rugged than an instrument employing an oscillating grating and also it is less expensive than an oscillating grating instrument. In an instrument with a fixed grating, it is preferable to use silicon photodetectors in the detector array in order to achieve the desired resolution in the detection. However, silicon detectors are effective to detect light only below 1100 nm and accordingly the array silicon photodetectors should be arranged to detect this portion of the spectrum dispersed by the fixed grating.

When a conventional fiber-optic probe such as that shown in U.S. Pat. No. 5,166,756 or that shown in U.S. Pat. No. 5,351,322 is used to apply infrared light to a particulate sample and receive light reflected back from the sample in the range of 500 nm to 1100 nm, an excessive amount of spectrally reflected light will be received by the optic-fibers of the probe arranged to received the reflected light. This excessive spectrally reflected light travels from the transmitting fibers to the receiving fibers at or near the interface between the probe and the sample. The transmission of this excessive spectrally reflected light from the transmitting fibers to the receiving fibers is called the light pipe effect. The excessive spectrally reflected light in the 500 to 1100 nm range washes out or overwhelms the received light diffusely reflected from the sample and prevents accurate measurements of the absorption of the sample.

This problem may be overcome by using a probe which transmits the light through a sample instead of detecting the light reflected from the sample wherein the sample is made sufficiently thick that all of the light passing through the sample constitutes diffusely reflected forward scattered light. However, a probe designed to measure light transmitted through a particulate sample is much more difficult to use in the field than a probe designed to measure reflected light because a sample holder must be carefully filed with a sample for each measurement to ensure that the sample through which the light is transmitted is of a consistent density for each measurement and so that no air pockets exist in the sample. In contrast, it is much easier to use a reflectance measuring probe which can be simply inserted into the sample and reflectance measurements taken.

Accordingly, there is a need for an infrared analysis instrument with a fixed grating which can make measurements from a particulate sample by a simple insertion of the probe into the sample without the measurements being adversely effected by spectrally reflected light.

SUMMARY OF THE INVENTION

In accordance with the invention, the problems described above are overcome by using a probe in which the central fibers of the probe are used to transmit light into the sample and a ring of receiving fibers surrounding the central transmitting fibers receive light reflected back from the sample. In accordance with the invention, the distal ends of the ring of receiving fibers are set back from the distal ends of the transmitting fibers so that light transmitted into the sample from the transmitting fibers and reflected by the sample must travel through a substantial amount of the sample to get to the ring of receiving fibers. As a result, all the spectrally reflected light will be attenuated to zero and all of the light received by the receiving fibers will be diffusely reflected light, which will be attenuated at each wavelength in accordance with the absorbance of the sample.

In the instrument of the invention, the light received by the ring of receiving optic fibers is transmitted through an entrance slit of a housing to irradiate a fixed grating contained by the housing. The grating disperses the received light into a spectrum and an array of silicon photodetectors are positioned to detect narrow wavelength bands of the spectrum in the range of 500 to 1100 nm. From the signals generated by the silicon photodetectors, the material of the particulate sample can be precisely identified or accurately analyzed by mathematical processing.

Because of the design of the probe, which can be simply inserted into the sample to make a measurement, the received light analyzed by the instrument is devoid of spectrally reflected light and an accurate analysis or identification of the particulate material can be made. Because the instrument employs a fixed grating to disperse the light, the instrument is rugged and is relatively inexpensive.

DESCRIPTION OF A PREFERRED EMBODIMENT

Figure 1:
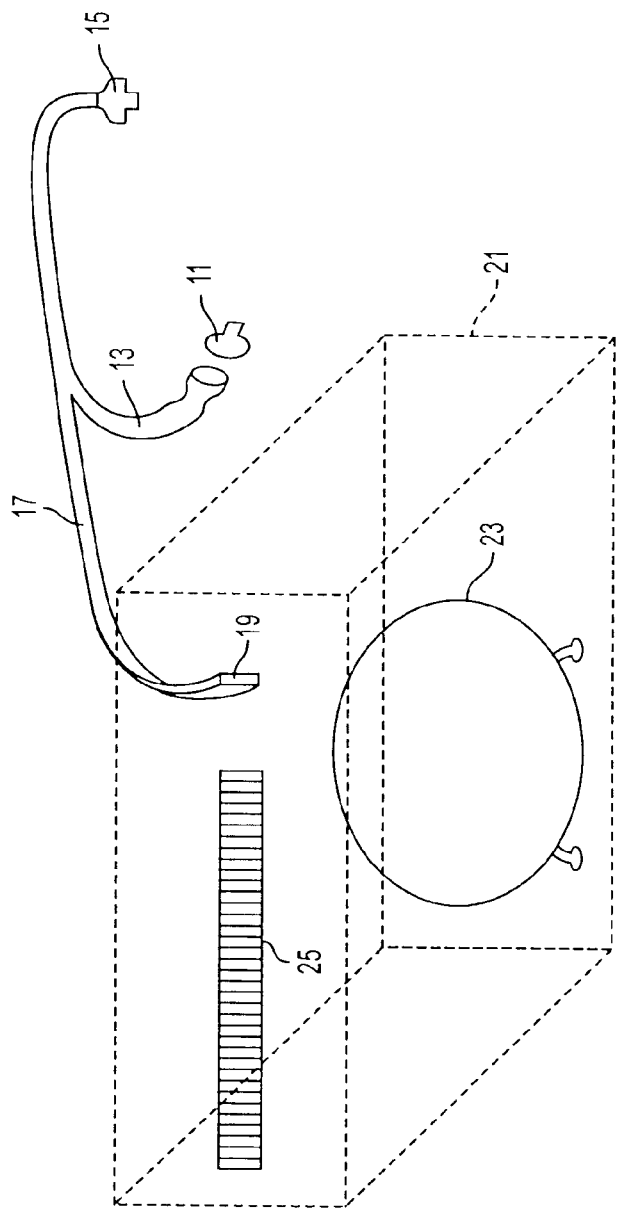
FIG. 1 is a schematic illustration of an instrument in accordance with the present invention.

In the instrument of the present invention, a near infrared light source 11 introduces broad band near infrared light, including the range 500 nm to 1100 nm, into an optical cable 13 designed to transmit the near infrared light. The optical fibers of the cable 13 transmit the near infrared light to a probe 15, which is designed to be inserted into a particulate sample. The probe 15 has both fibers for transmitting light into the sample and fibers for receiving light reflected from the sample. The optical fibers receiving light reflected from the sample are also designed to transmit NIR. The NIR is carried by the optic fibers through a cable 17 to an entrance slit 19 in the wall of a housing 21 of a spectrophotometer, in which fixed optical grating 23 is mounted. The entrance slit 19 is defined by the shape of the set of proximal ends of the receiving optic fibers which extend through the wall of the housing 21. The infrared light received from the sample and carried by the receiving fibers, through the cable 17 is emitted from the proximal ends of the fibers at the entrance slit 19 to irradiate the grating 23. The grating 23 disperses the incident light into an infrared spectrum directed toward an array of abutting silicon photodetectors 25 mounted on the wall of the housing 21. The silicon detectors 25 are positioned on the housing wall to detect the infrared spectrum throughout the range of 500 nm to 1100 nm. Each silicon detector is sized to detect a portion of the spectrum 2 nanometers in width. Accordingly the array includes 300 photodetectors.

Figure 2:
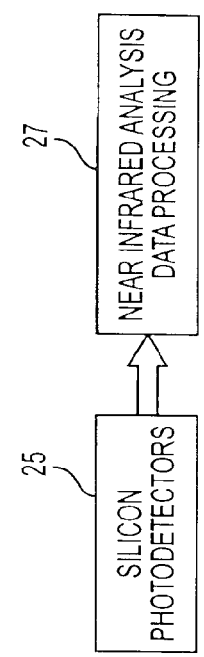
FIG. 2 is a block diagram illustrating the electronics of the instrument of the present invention.
Figure 3:
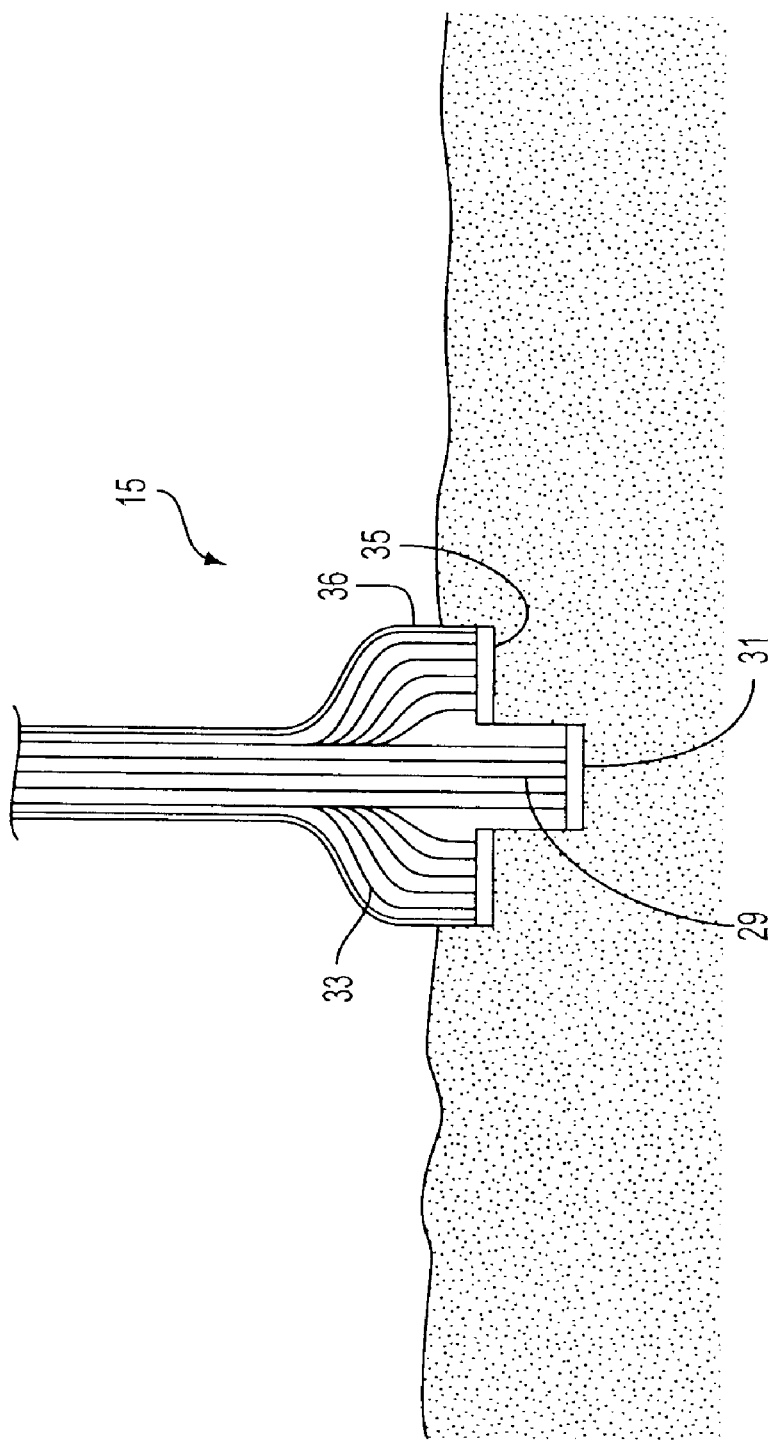
FIG. 3 is an axial sectional view of the probe employed in the instrument of the present invention, showing the probe inserted into a particulate sample

As shown in FIG. 2, the signals generated by the photodetectors 25 in response to the intensities of the narrow bandwidth light detected by each photodetector are transmitted to an NIR spectral analysis data processor 27. The processor 27 analyzes the received signals to identify the sample material, or to determine the percentage composition of its constituents, or to determine the value of a functional characteristic of the material by methods well known in the art. When the material of the sample is being identified, the absorbance spectrum obtained from the unknown sample is matched against spectrum from a library of known samples to determine the identity of the sample such as by the method disclosed in U.S. Pat. No. 5,822,219, issued Oct. 13, 1998, invented by Xiaolin Chen et al. If the sample is to have its percentage constituents determined or to have a functional value determined, the coefficients of an equation expressing the quantity or value being determined as a function of NIR absorbances, are computed from the spectra obtained from samples for which the quantity or value is known by means of a statistical technique such as multiple regression or by least squares. These coefficients are then used with the measurements obtained from the unknown material in the equation to determine the value of the functional characteristic or a percentage constituent of the unknown material.

As shown in FIG. 2, the probe 15 of the invention comprises an offset design wherein a central set of fibers 29 consists of the fibers in the cable 13 carrying light transmitted from the infrared source 11. The set of fibers 29 project from the distal end of the probe 15 and terminate in a face plate 31. A second set of fibers 33 are formed in a ring around the fiber 29 and consist of the fibers in a cable 17 which carry light reflected from the sample to the entrance slit 19. The distal ends of the optic fiber set 33 terminate in face plate 35 which is set back from the face plate 31. Thus the distal ends of the optic fibers 33 receiving reflected light from the sample are set back from the distal ends of the optic fibers 29 transmitting light into the sample. A sheath 36, which encloses the set of fibers 33, has its distal end terminate at the faceplate 35.

In use, the fiber optic probe 15 is inserted into a particulate sample 37 so that the face plate 31 is well below the surface of the sample and the face plate 35 is at or below the surface of the sample 37. When the probe is properly inserted in the sample, the material of the sample will completely fill the area around the outside of the projecting set of fibers 29 and between the edge of the faceplate 31 and the faceplate 35. When light from the near infrared light source 11 passes through the optic fibers 29 into the sample 37 it will be back scattered from the sample toward the distal ends of the optic fibers 33. The back scattered light will travel through the sample by forward scattering and be received by the optic fibers 33. By making the dimension of the offset between the distal ends of the optic fibers 29 and the optic fibers 33 large enough, substantially all of the light received by the optic fibers 33 will be light diffusely deflected by the sample and thus will be attenuated throughout the spectrum of received light in accordance with the absorbance of the sample. In this manner, an absorbance spectrum is obtained from the sample without any noise in the spectrum caused by spectrally reflected light. As a result an accurate identification of a material or an accurate analysis of the material can be obtained.

In the preferred embodiment, the dimension of the offset is made large enough that substantially all of the spectrally reflected light is eliminated from the light received by the set of receiving fibers 33. It will be apparent that any substanted offset will reduce the spectrally reflected light and thereby be an improvement over the prior art.

In the preferred embodiment, the set of fibers 29 are used to transmit light into the sample and the set of fibers 33 are used to receive the diffusely reflected light from the sample. However the roles of these two sets fibers could be reversed wherein the fibers 33 are used to transmit light into the sample and the fibers 29 are used to receive the diffusely reflected light. In such an arrangement, the light transmitted into the sample by the fibers 33 will be forward scattered to an area near the distal ends of the fibers 29 and then be back scattered to the fibers 29.

In the preferred embodiment, one set of optic fibers are formed in a ring around the other set and are set back from the other set. Other offset arrangements may be employed such as having the distal ends of the transmitting fibers occupy a semi-circular half of the probe end and having the offset distal ends of the receiving fibers occupy the other half of the probe end.

These and other modifications may be made to the above described preferred embodiment of the invention without departing from the spirit and the scope of the invention which is defined in the appended claims.

What is claimed:

1. An infrared analysis instrument comprising first and second sets of optical fibers, the distal ends of said first and second sets of optical fibers being formed into a probe for inserting into a particulate sample, an infrared light source arranged to introduce a near infrared light into the proximal ends of said first set of optical fibers to introduce said near infrared light into a particulate sample through the distal ends of said first set of optic fibers, the distal ends of said first and second set of optical fibers being offset from one another so that light introduced into said sample through said first set of optical fibers is diffusely transmitted through said sample to be received by the distal ends of said second set of optic fibers, a spectrophotometer positioned to receive the diffusely reflected light transmitted through said second set of optic fibers and detect the intensity of narrow band components of the spectrum of the near infrared light transmitted from the distal ends of said second set of optic fibers through said second set of optic fibers to said spectrophotometer.

2. An infrared analysis instrument as recited in claim 1 wherein the distal ends of one of said first and second sets of fiber optic fibers is centrally located in said probe and the distal ends of the other one of said first and second sets of optic fibers is arranged in a ring around the distal ends of said first set of optic fibers.

3. An infrared analysis instrument as recited in claim 2 wherein the distal ends of said second set of fibers are set back from the distal ends of said first set of fibers.

4. An infrared analysis instrument as recited in claim 1 wherein the distal ends of said second set of fibers are set back from the distal ends of said first set of fibers.

5. An infrared analysis instrument as recited in claim 1 wherein said spectrophotometer comprises a fixed grating positioned to be irradiated by light transmitted through said second set of fibers and an array of photodetectors positioned to detect narrow band width components of the spectrum dispersed by said grating.

6. An infrared analysis instrument as recited in claim 5 wherein said array of photodetectors are arranged to detect the spectrum of said near infrared light transmitted to said spectrophotometer in the range of 500 to 1100 nm, said photodetectors comprising silicon photodetectors.

7. An infrared analysis instrument as recited in claim 1 wherein said spectrophotometer comprises an array of photodetectors each arranged to detect a narrow band component of a dispersed spectrum, said spectrophotometer further comprising an optical dispersing element to disperse the near infrared light received through said second set of optic fibers into a spectrum dispersed over said array of photodetectors.

8. A infrared analysis instrument as recited in claim 7 wherein said array of photodetectors is arranged to detect the spectrum in the range of 500 to 1100 nm and wherein said photodetectors comprise silicon photodetectors.

9. A probe for an instrument measuring infrared absorbance of a particulate sample comprising a first set of optic fibers designed to transmit near infrared in the range of 500 to 1100 nm, a second set of optic fibers designed to transmit infrared light in the range of 500 to 1100 nm, the distal ends of said second set of optic fibers forming a ring around the distal ends of said first set of optic fibers to form said probe, the distal ends of said second set of optic fibers being set back from the distal ends of said first set of optic fibers, a sheath enclosing said second set of optic fibers said sheath having a distal end terminating at the distal ends of said second set of optic fibers.

10. A method of measuring the absorbance of a particulate material comprising inserting a fiber optic probe into said particulate material, said probe comprising a first set of optic fibers and a second set of optic fibers, the distal ends of said second set of optic fibers being offset from the distal ends of said first set of optic fibers, introducing near infrared light into said sample through said first set of optic fibers, receiving infrared light diffusely reflected by said sample into the distal ends of said second set of optic fibers, and measuring the intensity of the light transmitted through said second set of optic fibers.

11. A method as recited in claim 10 wherein the distal ends of said second set of optic fibers is set back from said first set of optic fibers so that light introduced into said sample through the distal ends of said first set of optic fibers is backward scattered from said sample and then forward scattered through said sample into the distal ends of said second set of optic fibers.

12. A method as recited in claim 10 further comprising dispersing the light received into the distal ends of said second optic fibers into a spectrum, and detecting narrow band components of said spectrum.

13. A method as recited in claim 12 wherein said narrow band components of said spectrum are detected by an array of silicon photodetectors positioned to detect said spectrum in the range from 500 nm to 1100 nm.

* * * * *